United States Patent [19]
Mille et al.

[11] Patent Number: 6,026,778
[45] Date of Patent: Feb. 22, 2000

[54] METHOD AND DEVICE FOR DECOKING A COMBUSTION CHAMBER OF A DIESEL ENGINE

[75] Inventors: Guy Mille, Echalas; Joseph Cellier, Venissieux, both of France

[73] Assignee: Elf Antar France, France

[21] Appl. No.: 09/123,315

[22] Filed: Jul. 28, 1998

[30] Foreign Application Priority Data

Jul. 29, 1997 [FR] France .................................. 97 09649

[51] Int. Cl.⁷ .................................................. F02B 77/04
[52] U.S. Cl. .................................. 123/198 A; 123/78 D; 73/35.02
[58] Field of Search ............................. 123/78 D, 198 A, 123/435; 73/35.02

[56] References Cited

U.S. PATENT DOCUMENTS

| | | | |
|---|---|---|---|
| 2,843,645 | 7/1958 | Sigworth et al. | 123/198 A |
| 3,469,954 | 9/1969 | Hoffman | 44/2 |
| 5,457,985 | 10/1995 | Cellier et al. | 73/35.02 |

FOREIGN PATENT DOCUMENTS

| | | |
|---|---|---|
| 2702004 | 9/1994 | France . |
| 1270838 | 6/1968 | Germany . |

*Primary Examiner*—Tony M. Argenbright
*Assistant Examiner*—Brian Hairston
*Attorney, Agent, or Firm*—Bacon & Thomas, PLLC

[57] ABSTRACT

The invention relates to the measuring of the cetane number of fuels supplied to diesel engines. According to the invention, the combustion chamber of a diesel engine for measuring the cetane number of a fuel is decoked by creating, between two measurement cycles, for 80 to 160 seconds, strong turbulence in the gases inside the combustion chamber. The invention finds its application in research laboratories, test laboratories and the units which manufacture these fuels in crude oil processing plants.

3 Claims, 2 Drawing Sheets

METHOD AND DEVICE FOR DECOKING A COMBUSTION CHAMBER OF A DIESEL ENGINE

TECHNICAL FIELD

The present invention relates to a method and to a device for decoking a combustion chamber of a diesel engine, this engine being intended for measuring the cetane number of fuels supplied to diesel engines.

It finds its application in research laboratories, test laboratories and the units which manufacture these fuels in crude oil processing plants.

STATE OF THE PRIOR ART

A method for measuring the cetane number of fuels supplied to diesel engines and a device for implementing this method are described in Patent FR 2 701 118.

According to this method, the value of the cetane number of a fuel supplied to diesel engines is measured by comparing it with a reference fuel whose cetane number is known.

As these supply and reference fuels have respective spontaneous-ignition lags, this method consists of using a measurement diesel engine turning over at a constant speed and supplied in turn with the said reference fuel and with the said supply fuel, the said measurement engine having a constant compression ratio and a constant injection advance, and of calculating the cetane number of the supply fuel on the basis of the value of the cetane number of the reference fuel and on the basis of the values of spontaneous-ignition lags measured respectively with the reference fuel and with the supply fuel.

The known equipment used for implementing this method essentially comprises:

- a single-cylinder engine with a variable volumetric compression ratio,
- an injection pump equipped with a micrometric means that allows the injection advance to be adjusted manually,
- a fuel injector,
- a piston plunger, the position of which can be altered by acting on a control rod, which allows the compression ratio to be adjusted,
- means for measuring the spontaneous-ignition lag of the fuels with which the engine can be supplied.

The results obtained with this method and this equipment are not very reliable.

Also, a significant drift in measurements is observed over time, this being particularly troublesome when the motor is used on the line, for continuously measuring the cetane number of a fuel as it is being produced.

These discrepancies and this drift over time are due, in particular, to the solid residues of combustion of the fuel known as coke which becomes deposited on the walls of the combustion chamber of the engine, that is to say the volume in which compression of the air-fuel mixture takes place.

One known method for removing these coke deposits consists of periodically carrying out the following operations:

- removing the injector and the piston plunger,
- mechanically removing the coke which has been deposited on the walls of these two components using appropriate tools, such as brushes,
- carefully cleaning these two components,
- and finally re-fitting them, every 50 operating hours.

The time taken to complete these operations is about one hour, during which the engine is not available to take measurements. The frequency and duration of this non-availability are a drawback when the engine is being used in a laboratory. They make this method inapplicable when the engine is used for the in-line measurement of the cetane number of a fuel as it is being produced. This is because the results of this measurement are used in a process for regulating and controlling the quality of the manufactured product which cannot tolerate being interrupted for one hour.

The reliability of the results obtained with this method is mediocre. For example, for a fuel with a cetane number of 49, reproducibility errors of the order of 3.8 are observed.

What is more, this method requires the intervention of a qualified mechanic and cannot be automated.

SUMMARY OF THE INVENTION

The object of the present invention is precisely to overcome these drawbacks and in particular to provide an automatic device and method for decoking an engine for measuring the cetane number of fuels for diesel engines.

This method and this device can be used with equal ease in the case of laboratory engines and in the case of engines operating in line in fuel-production units.

To this end, the present invention provides a method for decoking a combustion chamber of a diesel engine, this engine being intended for measuring the cetane number of a supply fuel by comparison with the known cetane number of a reference fuel, the said fuels being injected in turn into the combustion chamber which has already been filled with air in order to create a flammable mixture, the said method comprising creating, between two measurement cycles, for 80 to 160 seconds, strong turbulence in the flammable mixture and gases resulting from its combustion so as at least partially to detach the solid residues of combustion that have been deposited on the walls of the combustion chamber.

This detaching effect is the result of the increase in the speeds at which the gases flow through the combustion chamber, especially near the walls, compared with the speeds of the gases in stable operating regime, which characterizes the turbulence created.

According to another feature of the method of the invention, with the diesel engine turning over at a constant speed, with a predetermined injection advance and a given compression ratio, the fuel with which the engine is supplied having an initial spontaneous-ignition lag, it consists of carrying out the following steps:

- decreasing the compression ratio in order to obtain a spontaneous-ignition lag of between 1.05 and 1.2 times the initial self-ignition lag after a length of time of between 20 and 40 seconds,
- adjusting the compression ratio in order to keep the spontaneous-ignition lag at the value reached in the previous step, for 1 to 10 seconds,
- increasing the compression ratio in order to obtain a spontaneous-ignition lag of between 0.8 and 0.6 times the initial spontaneous-ignition lag after a length of time of between 40 and 80 seconds,
- adjusting the compression ratio in order to keep the spontaneous-ignition lag at the value reached in the previous step, for 1 to 10 seconds,
- decreasing the compression ratio in order to return the spontaneous-ignition lag to its initial value in a length of time between 20 and 40 seconds.

The present invention also provides a device for decoking a combustion chamber of a diesel engine, this engine being intended for measuring the cetane number of a supply fuel by comparison with the known cetane number of a reference fuel, comprising a combustion chamber already filled with air and into which the said fuels are injected in order to create a flammable mixture, characterized in that it additionally comprises means for creating, between two measurement cycles, for 80 to 160 seconds, strong turbulence in the flammable mixture and gases resulting from its combustion, so as at least partially to detach the solid residues of combustion that have been deposited on the walls of the combustion chamber.

According to another feature of the device of the invention, with the engine comprises:

- means for measuring the spontaneous-ignition lag of the said fuels, which means are connected to one output of a pressure sensor,
- a controllable piston plunger, the position of which determines the compression ratio, the engine turning over at constant speed, with a predetermined injection advance and a given compression ratio, the fuel supplied to the engine having an initial spontaneous-ignition lag, the means for creating strong turbulence in the flammable mixture and gases resulting from its combustion comprise:
- a processing unit connected to one output of the means of measuring the spontaneous-ignition lag and to memory-storage means,
- an actuator electrically connected to one output of the processing unit and mechanically connected to a controller of the piston plunger, in order quickly to vary the spontaneous-ignition lag of the fuel supplied to the engine.

According to a last feature of the device of the invention, the processing unit produces a control signal for the actuator to make it perform the following operation:

- altering the position of the piston in order to obtain a spontaneous-ignition lag of between 1.05 and 1.2 times the initial spontaneous-ignition lag after a length of time of between 20 and 40 seconds,
- adjusting the position of the piston to keep the spontaneous-ignition lag at the value reached at the end of the previous operation, for 1 to 10 seconds,
- altering the position of the piston in order to obtain a spontaneous-ignition lag of between 0.8 and 0.6 times the initial spontaneous-ignition lag after a length of time of between 40 and 80 seconds,
- adjusting the position of the piston in order to keep the spontaneous-ignition lag at the value reached at the end of the previous operation, for 1 to 10 seconds,
- altering the position of the piston in order to return the spontaneous-ignition lag to its initial value in a length of time of between 20 and 40 seconds.

Thanks to the invention, the decoking operation makes the engine unavailable for a relatively short length of time, of between 80 and 180 seconds, which is entirely acceptable for use of an engine in a laboratory or for the in-line measurement of the cetane number of a fuel as it is being produced.

Thanks also to the invention, the frequency with which the injector and the piston plunger need to be removed for cleaning can be reduced, as, therefore, to the same extent can be the number of interventions by a specialist mechanic, while at the same time improving the reliability of the results of the measurements.

An additional advantage of the method of the invention is that it can be automated.

BRIEF DESCRIPTION OF THE DRAWINGS

The invention will be better understood with the aid of the following description, with reference to the appended drawings, in which.

DETAILED DESCRIPTION OF THE INVENTION

In general, the method and the device of the invention are used for decoking engines intended for measuring the cetane number of fuels for diesel engines.

Figure 1:
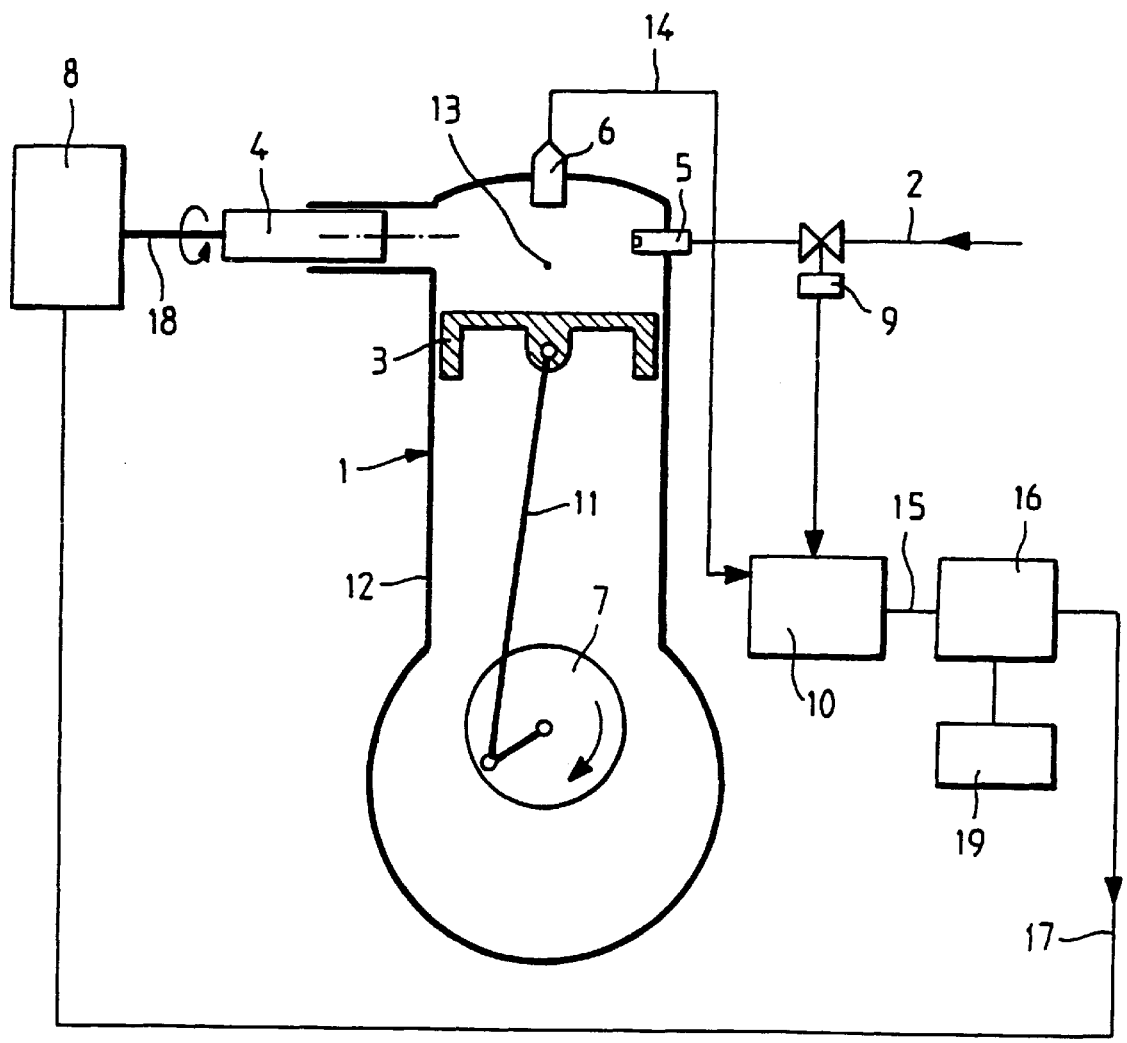
FIG. 1 diagrammatically depicts the main components of an engine for measuring the cetane number of fuels for diesel engines and the associated components for decoking it in accordance with the description of the invention.

According to the embodiment depicted in FIG. 1, the device of the invention comprises:

- a single-cylinder diesel engine 1, of Waukhesa make, supplied with fuel by a line 2 comprising a cylinder 12, a piston 3, connected to a crankshaft 7 by a connecting rod 11, a piston plunger 4, the position of which can be adjusted by a rotary control 18, a fuel injector 5,
- a sensor 9 for detecting the moment of injection, which supplies an electric pulse at the moment the fuel is injected into the engine,
- a sensor 6 for measuring the pressure in the combustion chamber 13 and which supplies on one output 14 an electric signal that represents this pressure,
- means 10 for measuring the spontaneous-ignition lag for the fuel supplied to the engine, these means being connected to the output 14 of the sensor 6 and to one output of the sensor 9.
- an actuator 8 comprising a step-controlled motor which makes 1 revolution for 200 control steps, coupled to reduction gearing in the ratio 1/20, the output shaft of which is mechanically connected to the controller 18 for controlling the rotation of the piston plunger 4,
- a processing unit 16 connected to one output 15 of the means 10 of measuring the spontaneous-ignition lag and which delivers on one output 17 a control signal for the actuator 8 to which it is connected,
- memory-storage means 19 associated with the processing unit 16 to which they are connected.

The compression ratio of the engine can be adjusted by altering the position of the piston plunger 4. Each revolution of the rotation controller 18 corresponds to a longitudinal displacement of the piston 4 which alters the volume of the combustion chamber 13 and therefore the compression ratio by a determined amount.

A cycle of measuring the cetane number of a fuel whose cetane number is to be determined can be broken down into two parts; a first part, during which the engine is supplied with a reference fuel of known cetane number approximately equal to 49, and a second part, during which the motor is supplied with the fuel whose cetane number, close to that of the reference fuel, is to be determined.

This measurement cycle takes place continuously as follows.

In the first part of the measurement cycle, with the engine 1 turning over at constant speed, for example 900 revolutions per minute, the injection advance being kept equal to 15° crank angle, during a first so-called set-up phase, the compression ratio is adjusted automatically in order to obtain a predetermined spontaneous-ignition lag for the reference fuel equal to 14° crank angle.

This automatic adjustment of the compression ratio takes place as follows:

The processing unit 16, which on one input connected to the output 15 of the means 10 of measuring the spontaneous-ignition lag receives an electric signal that represents the spontaneous-ignition lag, executes a first program stored in the memory-storage means 19, which compares the value of this signal with a predetermined reference value equal to 14°±0.2° and, using a conventional regulation algorithm, calculates the value of an action signal which is supplied on the output 17.

This signal is applied to the input of the actuator 8 which alters the position of the piston 4 until the spontaneous-ignition lag is equal to the predetermined reference value.

During a second phase of the first part of the measurement cycle, without altering the position that the piston plunger reached at the end of the set-up phase, the mean value of the spontaneous-ignition lag of the reference fuel is measured for about 55 seconds.

In the second part of the measurement cycle, with the motor supplied with the supply fuel whose cetane number is to be determined, without altering the engine compression ratio, that is to say without altering the position reached by the piston plunger at the end of the set-up phase, the running of the engine is stabilized during a first phase and then, during a second phase, the mean value of the spontaneous-ignition lag of the supply fuel is measured for about 55 seconds.

The cetane number of the supply fuel is calculated using the following known formula:

$$Icx = Icref + K(Dmes - Dref)$$

in which:

Icx is the value of the cetane number of the supply fuel,

Icref is the value of the cetane number of the reference fuel,

Dref is equal to the mean value of the spontaneous-ignition lag of the reference fuel as measured during the second phase of the first part of the measurement cycle, Dmes is equal to the mean value of the spontaneous-ignition lag of the fuel whose cetane number is to be determined, as measured during the second phase of the second part of the measurement cycle, K is a constant determined experimentally by earlier calibration work on the engine using fuels whose cetane number is precisely known.

As the cetane numbers of the reference fuel and of the supply fuel are close to each other, in identical engine-operating conditions, these two fuels have similar spontaneous-ignition lags.

The method of decoking the diesel engine according to the invention and implemented by the device depicted in FIG. 1 consists in producing, within the combustion chamber of the engine, turbulence in the flammable fuel-air mixture and in the resulting combustion gases.

This turbulence is created periodically every three measuring cycles, for example at the end of the second part of the third measuring cycle, as follows, the engine being supplied with the reference fuel. The processing unit 16 executes a second program stored in the memory-storage means 19 and which has the effect of triggering the following sequence of steps:

delivering on the output 17 of the processing unit an electric signal for controlling the actuator 8 in such a way as to reduce the compression ratio so that the spontaneous-ignition lag of the supply fuel reaches the value of about 16°, after a length of time equal to about 25 seconds, calculating and delivering on the output 17 of the processing unit, a signal for keeping the self-ignition lag at this 16° value for about 5 seconds, delivering on the output 17 of the processing unit, an electrical signal for controlling the actuator 8 so as to increase the compression ratio so that the spontaneous-ignition lag of the supply fuel reaches the value of about 10° after a length of time of about 40 seconds, calculating and delivering on the output 17 of the processing unit a signal for keeping the spontaneous-ignition lag at this 10° value for about 5 seconds, delivering on the output 17 of the processing unit, an electric signal for controlling the actuator 8 in such a way as to reduce the compression ratio so that the spontaneous-ignition lag of the supply fuel reaches the value of about 14° after a length of time of about 25 seconds.

Once this sequence of events has been completed, a series of three further measuring cycles is begun, at the end of which the decoking steps are performed again.

The reproducibility of the results of the measurement of cetane number obtained is within 2.5 points, with the injector and piston plunger being removed and cleaned every 100 operating hours.

According to another embodiment of the invention, the decoking steps take place following the first part of a measuring cycle, during which the engine is supplied with a reference fuel.

The two embodiments of the invention described hereinabove are given by way of non-limiting example.

The frequency of decoking will easily be adjusted experimentally to suit the nature of the fuels, their tendencies to soil the engine and the drift in supply fuel cetane number measurement deemed acceptable for a given application.

Figure 2:
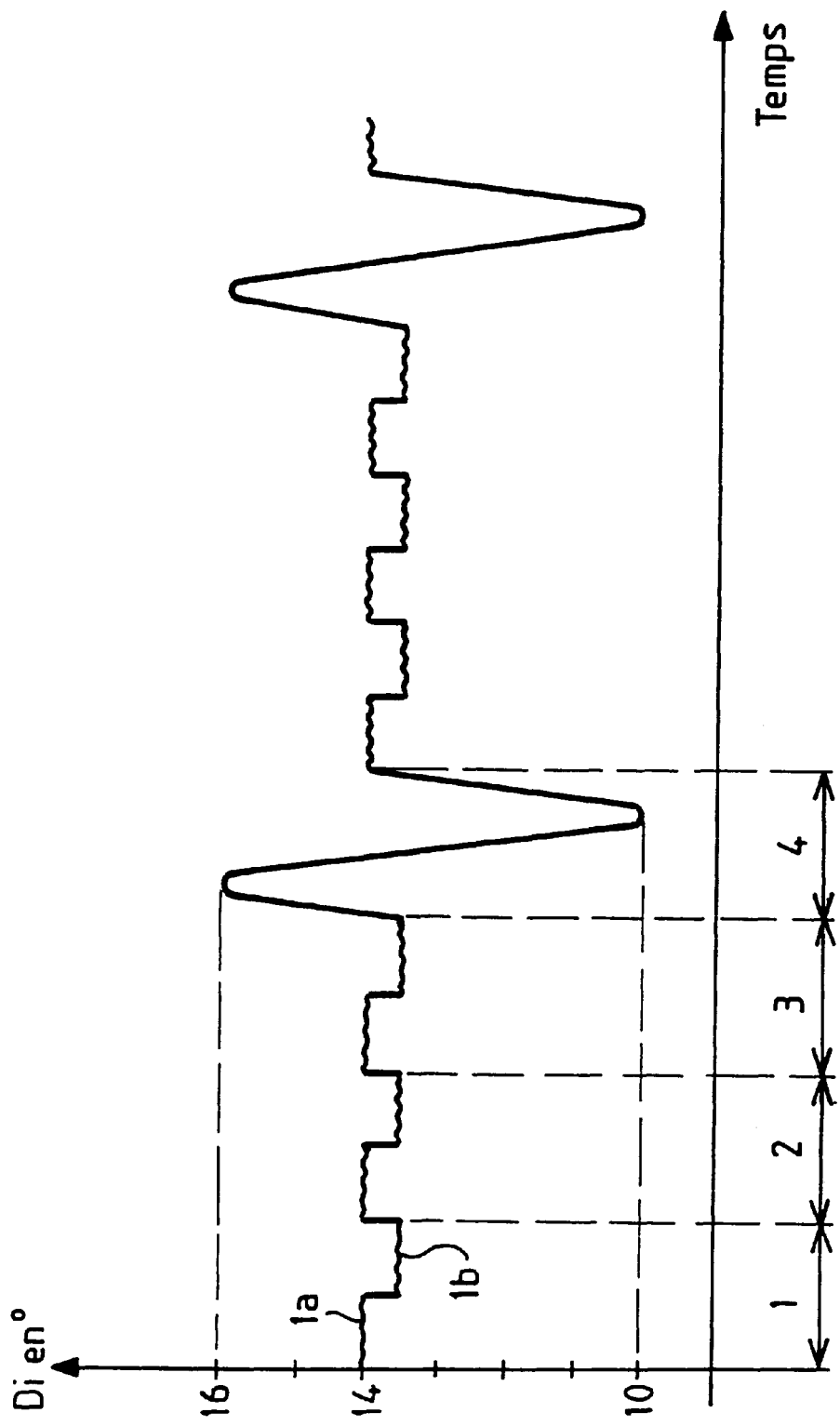
FIG. 2 depicts the change over time of the spontaneous-ignition lag of the fuel supplied to a diesel engine for the in-line measurement of the cetane number of a fuel in accordance with the description of the invention.

FIG. 2 depicts the change in spontaneous-ignition lag Di for the fuel supplied to the engine, expressed in degrees crank angle as a function of time in accordance with the first embodiment described earlier.

The time intervals 1, 2 and 3 correspond to three successive measurement cycles, each of them comprising a first part during which the engine is supplied with the reference fuel of known cetane number, and a second part, during which the engine is supplied with the supply fuel whose cetane number is to be determined. For the measuring cycle which takes place during the time interval 1, these two parts of the measuring cycle are identified 1a and 1b respectively.

The steps of the decoking method of the invention take place during the time interval 4, during which the fluctuations in the spontaneous-ignition lag for the fuel supplied to the engine and brought about by the variations in engine compression ratio, in accordance with the method of the invention, can be clearly seen.

We claim:

1. Method for decoking a combustion chamber of a diesel engine used for measuring the cetane number of a reference fuel, by injecting the fuels sequentially into the combustion chamber previously filled with air in order to create a flammable mixture, the said decoking method comprising:

decreasing the compression ratio in the diesel engine in order to obtain a spontaneous-ignition lag of between 1.05 and 1.2 times the initial self-ignition lag after a length of time of between 20 and 40 seconds, adjusting the compression ratio in order to keep the spontaneous-ignition lag at the value reached in the previous step, for 1 to 10 seconds, and increasing the compression ratio in order to obtain a spontaneous-ignition lag of between 0.8 and 0.6 times the initial spontaneous-ignition lag after a length of time of between 40 and 80 seconds, adjusting the compression ratio in order to keep the spontaneous-ignition lag at the value reached in the previous step, for 1 to 10 seconds, decreasing the compression ratio in order to return the spontaneous-ignition lag to its initial value in a length of time between 20 and 40 seconds, whereby, between two measurement cycles, strong turbulence in the flammable mixture and the gases resulting from the combustion of the flammable mixture are created so as to at least partially detach the solid residues of combustion that have been deposited on the walls of the combustion chamber.

2. Device for decoking a combustion chamber of a diesel engine used for measuring the cetane number of a supply fuel by comparison with the known cetane number of a reference fuel, comprising a combustion chamber filled with air and into which the said fuels are injected in order to create a flammable mixture and means for creating, between two measurement cycles, strong turbulence in the flammable mixture and the gases resulting from the combustion of the flammable mixture, so as to at least partially detach the solid residues of combustion that have been deposited on the walls of the combustion chamber, wherein the engine comprises:

means for measuring the spontaneous-ignition lag of said fuels, which means are connected to one output of a pressure sensor in the combustion chamber and to a sensor for detecting the moment of injection, and a controllable piston plunger, the position of which determines the compression ratio of the engine, and wherein the means for creating strong turbulence in the flammable mixture and gases resulting from its combustion comprises:

a processing unit connected to one output of the means for measuring the spontaneous-ignition lag and to memory-storage means, and an actuator electrically connected to one output of the processing unit and mechanically connected to a controller of a piston plunger in order to quickly vary the spontaneous-ignition lag of the fuel supplied to the engine.

3. Device according to 2, wherein the processing unit produces a control signal for the actuator to make it perform the following operations:

altering the position of the piston in order to obtain a spontaneous-ignition lag of between 1.05 and 1.2 times the initial spontaneous-ignition lag after a length of time of between 20 and 40 seconds, adjusting the position of the piston to keep the spontaneous-ignition lag at the value reached at the end of the previous operation, for 1 to 10 seconds, altering the position of the piston in order to obtain a spontaneous-ignition lag of between 0.8 and 0.6 times the initial spontaneous-ignition lag after a length of time of between 40 and 80 seconds, adjusting the position of the piston in order to keep the spontaneous-ignition lag at the value reached at the end of the previous operation, for 1 to 10 seconds, and altering the position of the piston in order to return the spontaneous-ignition lag to its initial value in a length of time of between 20 and 40 seconds.

* * * * *